(12) United States Patent
Johnson

(10) Patent No.: US 7,306,811 B2
(45) Date of Patent: Dec. 11, 2007

(54) FUNGICIDE COMPOSITION BASED ON HALOSULPHONE IN PARTICULAR FOR PACKAGING

(76) Inventor: Richard C Johnson, 3, avenue Emile Accolas, 75007 Paris (FR)

( * ) Notice: Subject to any disclaimer, the term of this patent is extended or adjusted under 35 U.S.C. 154(b) by 470 days.

(21) Appl. No.: 10/415,462

(22) PCT Filed: Nov. 9, 2001

(86) PCT No.: PCT/FR01/03486

§ 371 (c)(1),
(2), (4) Date: Apr. 29, 2003

(87) PCT Pub. No.: WO02/37962

PCT Pub. Date: May 16, 2002

(65) Prior Publication Data

US 2004/0043060 A1    Mar. 4, 2004

(30) Foreign Application Priority Data

Nov. 10, 2000 (FR) .................................. 00 14455

(51) Int. Cl.
*A01N 25/34* (2006.01)
(52) U.S. Cl. ...................... 424/415; 424/404; 424/405; 424/406; 424/412; 424/413; 424/414; 514/647; 514/709
(58) Field of Classification Search ...................... None
See application file for complete search history.

(56) References Cited

FOREIGN PATENT DOCUMENTS

| JP | 50-046833 | * | 4/1975 |
| WO | WO 94/09209 | | 4/1994 |

OTHER PUBLICATIONS

Chemical Abstracts, vol. 83, No. 11, Patent Abstract of Japan No. 75 46833, Apr. 25, 1975.
Database WPI Section CH, Week 198519, Patent Abstract of Japan No. 60 054301, Mar. 28, 1985.

* cited by examiner

*Primary Examiner*—Neil S. Levy
(74) *Attorney, Agent, or Firm*—Renner, Kenner, Greive, Bobak Taylor & Webber

(57) ABSTRACT

A packaging sheet comprising a mixture of compound A

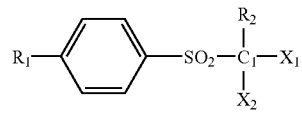

where $R_1$ may be an alkyl, alkoxy or alkylene radical having 1 to 6 carbon atoms; $X_1$ and $X_2$, identical or different, may be hydrogen or a halogen.
and compound B

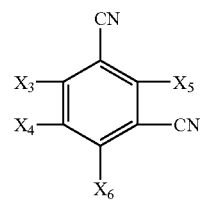

$X_3$, $X_4$, $X_5$, and $X_6$ being identical or different and selected from Cl, halogens or alkyl compounds having 1 to 6 carbon atoms or hydrogen;
the particle size of the mixture being less than 10 μm.

10 Claims, No Drawings

FUNGICIDE COMPOSITION BASED ON HALOSULPHONE IN PARTICULAR FOR PACKAGING

This invention relates to packaging sheets coated with a fungicidal composition, which provide protection over a long period for the packaged product, in respect of the growth of moulds. The invention relates particularly to the area of packaging soaps or food products, more particularly packaging or labels of paper or cardboard for products of this kind.

In this specification, the term "packaging sheet" also denotes a label.

A fungicide which is well known, for example in the area of soap packaging, is di-iodo-methyl-p-tolylsulphone, which is also known by the name of Amical (registered trademark). This compound, known as DIMPTS, is an excellent fungicide for application to packaging, more particularly soap packaging, and perfectly combats in the long term moulds which may form on packaging papers. However, this product has the disadvantage of being very expensive.

This invention relates to a packaging sheet, more particularly of paper, having excellent fungicidal properties, more particularly for packaging soap or food products and, more particularly, fungicidal properties as good as packaging sheets made on the basis of DIMPTS, but being much less expensive to produce, more particularly 2 to 3 times less expensive.

According to the present invention, a packaging sheet comprising a support made of packaging material surface coated on one of its sides with a coating of fungicidal composition, is characterised in that the fungicidal composition comprises a mixture
of compound A

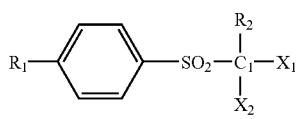

where $R_1$ is an alkyl, alkoxy or alkylene radical having 1 to 6 carbon atoms, $R_2$ being H, an alkyl or alkylene radical having 1 to 6 carbon atoms, $X_1$ being a halogen, more particularly iodine, bromine or chlorine, $X_2$ being an halogen, more particularly iodine, chlorine or bromine; and
of compound B of developed formula:

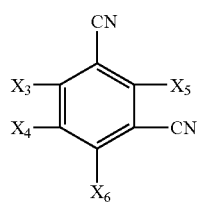

where $X_3$, $X_4$, $X_5$, $X_6$ which are identical or different may be selected from the halogens, alkyl compounds having 1 to 6 carbon atoms or hydrogen; and the particle size of the mixture being less than 10 μm, preferably less than 5 μm.

The preferred alkyl radicals have 1 to 3 carbon atoms, the methyl radical being particularly preferred.

According to a preferred embodiment of the invention, compound B is chlorotalonil or tetrachloroisophthalonitrile or 2,4,5,6 tetrachloro-1,3 benzene dicarbonitrile, and compound A is di-iodomethyl-p-tolyl-sulphone: (DIMPTS).

According to a preferred embodiment of the invention, the mixture comprises 10 to 70% by weight of DIMPTS and 90 to 30% by weight of chlorothalonil.

The packaging sheet according to the invention is less expensive because the fungicidal mixture is much less expensive than those already known for surface applications, and because the surface application reduces the amount thereof requiring to be applied.

Hitherto no-one had ever thought of, nor succeeded in, applying a suspension of this kind to paper, while its fungicidal properties have been known since 1975, The fact that a small particle size is provided enables such application while retaining a sufficient fungicidal effect in spite of the application solely to the surface.

The packaging sheet according to the invention is used particularly for packaging soap, food products, or as a label on packaging of this kind.

To prepare an example of a packaging sheet according to the invention, there may be mixed in the suspension agent, for example water or an alkanol, tetrachloroisophthalonitrile (or chlorothalonil) and di-iodomethyl-p-tolyl-sulphone (or Amical), in the proportion of 70% by weight of chlorothalonil and 30% by weight of DIMPTS, the composition of the aqueous suspension being such that it contains 41% of active material. The appearance of the mixture is a beige liquid, the density of which is between 1.24 and 1.28 and the pH between 5 and 8, while the particle size is between 1 and 4 microns. Also, a binder such as starch or a latex is added to the mixture in proportions by weight of 0.2 to 1.5 in relation to the mixture.

The mixture obtained can then be incorporated either in a coating mix or be added by means of a size press to a packaging paper. The recommended dose range is 500 to 4000 ppm based on the dry weight of the paper or on the size.

The packaging paper may have a weight between 40 $g/m^2$ and 150 $g/m^2$, while the protective surface coating is of a weight between 2 and 20 $g/m^2$, preferably between 5 and 15 $g/m^2$. In the case of a cardboard, the latter has a weight of between 150 $g/m^2$ and 350 $g/m^2$.

The following test was carried out. Two surfaces of a woodless industrial paper weighing 80 $g/m^2$ dry, having a 1-minute COBB value of 25 to 35, were brought into contact with six mushroom strains for 14 days under the quality test conditions of the standard AFNOR X 41 517: the strains used were *Aspergillus Sydowi*, *Aspergillus Versicolor*, *Cladosporium Herbarum*, *Cladosporium Sphaerospernum*, *Penicillium Citrinum* and *Penicillium Corylophilum*. At the end of this period, visual assessment of the development of moulds was noted using a code from 0 to 6+, the value 6+ being allocated to the untreated control, while the notation 0 corresponded to no development of the seeded moulds.

The COBB value is a measure of resistance to water.

| FUNGICIDES | ASSESSMENT OF DEVELOPMENT RECTO | ASSESSMENT OF DEVELOPMENT VERSO |
|---|---|---|
| Control $T_0$ | 6+ | 6+ |
| Chlorothalonil alone $T_1$ | 2+ | 2+ |

-continued

| FUNGICIDES | ASSESSMENT OF DEVELOPMENT RECTO | ASSESSMENT OF DEVELOPMENT VERSO |
|---|---|---|
| DIMPTS alone $T_2$ | 0+ | 0+ |
| Chlorothalonil + ZPT $T_3$ | 5+ | 2+ |
| DIMPTS + ZPT $T_4$ | 0+ | 0+ |
| Chlorothalonil + DIMPTS $T_5$ | 0+ | 0+ |

The fungicide solutions used in this test were prepared in the same way as mentioned above. With regard to the fungicide $T_1$, chlorothalonil was mixed in water. The fungicidal product $T_2$ was prepared on the basis of di-iodo-ethyl-p-tolyl-sulphone only. The fungicide $T_3$ was prepared from a mixture of chlorotalonyl and a zinc pyrithione. The fungicide $T_4$ was prepared from a mixture of Amical (di-iodomethyl-p-tolyl-sulphone, and zinc pyrithione. Finally the fungicide $T_5$ corresponds to the mixture given by way of example above according to the invention, i.e. a mixture of chlorotalonyl and di-iodo-methyl-p-tolyl-sulphone or Amical.

As will be seen from the Table, chlorothalonil alone is an average fungicide. Amical alone is an excellent fungicide. However it is very expensive.

Chlorothalonil mixed with zinc pyrithione does not give a good result. On the other hand, zinc pyrithione mixed with DIMPTS gives good results. However, zinc pyrithione is as expensive as DIMPTS. Mixed with. DIMPTS, chlorotalonyl gives a fungicide as effective as DIMPTS alone or as DIMPTS mixed with zinc pyrithione, two fungicides much less expensive to make than the fungicide used according to the invention.

The invention claimed is:

1. An assembly comprising an article and packaging sheet, said article being packaged in said packaging sheet, said packaging sheet comprising a mixture
   of di-iodomethyl-p-tolyl sulphone and
   of chlorothalonyl
   wherein said mixture is applied in the shape of a superficial layer on the sheet, wherein the superficial layer has a weight of between 2 and 15 $g/m^2$, and wherein said article is soap or a food product and wherein the particle size of the mixture is from 1 to 10 µm.

2. An assembly according to claim 1, characterized in that the particle size of the mixture is from 1 to 4 µm.

3. An assembly according to claim 1, characterized in that the mixture comprises a binder, comprising starch or a latex.

4. An assembly according to claim 1, characterized in that the mixture contains 10 to 70% by weight of (A) and 90% to 30% by weight of (B).

5. An assembly according to claim 1, characterized in that the packaging sheet is paper, having a weight between 40 $g/m^2$ and 150 $g/m^2$.

6. An assembly according to claim 1, characterized in that the packaging sheet is of cardboard, having a weight of between 150 $g/m^2$ and 350 $g/m^2$.

7. An assembly according to claim 3, characterized in that the ratio of binder to mixture by weight is between 0.2 and 1.5.

8. A method of making a packaging sheet from packaging material comprising the steps:
   providing a sheet of packaging material;
   mixing, in a suspension agent, di-iodomethyl-p-tolylsulphone and chlorothalonyl
   to obtain a mixture, wherein the particle size of the mixture is from 1 to 10 µm;
   depositing the mixture on one of the surfaces of the packaging sheet; and
   allowing to dry to evaporate the suspension agent, wherein said step of depositing further comprises deDositing the mixture on one of the surfaces of the packaging sheet in the form of a coating of 2 to 20 $g/m^2$.

9. A production method according to claim 8, further comprising the step of adding a binder to the mixture.

10. An assembly according to claim 8, wherein the particle size of the mixture is from 1 to 4 µm.

\* \* \* \* \*